US010610259B2

(12) United States Patent
Vogele

(10) Patent No.: US 10,610,259 B2
(45) Date of Patent: Apr. 7, 2020

(54) INSTRUMENT GUIDE

(71) Applicant: ISYS MEDIZINTECHNIK GMBH, Kitzbuhel (AT)

(72) Inventor: Michael Vogele, Schwabmunchen (DE)

(73) Assignee: ISYS MEDIZINTECHNIK GMBH, Kitzbuhel (AT)

( * ) Notice: Subject to any disclaimer, the term of this patent is extended or adjusted under 35 U.S.C. 154(b) by 23 days.

(21) Appl. No.: 14/438,823

(22) PCT Filed: Oct. 26, 2013

(86) PCT No.: PCT/EP2013/003224
§ 371 (c)(1),
(2) Date: May 24, 2016

(87) PCT Pub. No.: WO2014/063828
PCT Pub. Date: May 1, 2014

(65) Prior Publication Data
US 2016/0278806 A1 Sep. 29, 2016

(30) Foreign Application Priority Data
Oct. 26, 2012 (DE) .................... 20 2012 010 230 U

(51) Int. Cl.
*A61B 17/34* (2006.01)
*A61B 90/00* (2016.01)
(52) U.S. Cl.
CPC .. *A61B 17/3403* (2013.01); *A61B 2017/3407* (2013.01); *A61B 2090/3954* (2016.02); *A61B 2090/3966* (2016.02); *A61B 2090/3983* (2016.02)

(58) Field of Classification Search
CPC ............... A61B 17/3403; A61B 90/11; A61B 2090/3954; A61B 2090/3966; A61B 2090/3983; A61B 2090/3407
See application file for complete search history.

(56) References Cited

U.S. PATENT DOCUMENTS

| 3,477,429 A | * | 11/1969 | Sampson | ........... A61B 17/8866 606/86 R |
| 5,441,042 A | * | 8/1995 | Putman | .................... B25J 9/042 600/102 |
| 6,665,554 B1 | | 12/2003 | Charles et al. | |

(Continued)

OTHER PUBLICATIONS

International Search Report and Written Opinion issued in related International Patent Application No. PCT/EP2013/003224 dated Feb. 17, 2014.

*Primary Examiner* — Tuan V Nguyen
(74) *Attorney, Agent, or Firm* — Venable LLP; Michele V. Frank

(57) ABSTRACT

For variable use and simple construction of an instrument guide, particularly for inserting a puncture needle into patients, wherein the instrument guide (1) has a main body (2), which is mounted pivotably in a plurality of axes preferably on two adjusting arms (3, 4), according to the invention the instrument guide (1) has two or more guide cheeks (5), which are centrally adjustable and coupled to one another. This ensures that, when changing between instruments or needles of different thicknesses, the centre of the needle channel remains precisely on the target or central axis (6*a*).

12 Claims, 2 Drawing Sheets

(56) References Cited

U.S. PATENT DOCUMENTS

| | | | |
|---|---|---|---|
| 2003/0208207 A1* | 11/2003 | Layer | A61B 90/11 606/130 |
| 2003/0225422 A1* | 12/2003 | Mosnier | A61B 17/2812 606/151 |
| 2006/0149147 A1* | 7/2006 | Yanof | A61B 6/12 600/424 |
| 2008/0243106 A1* | 10/2008 | Coe | A61B 17/00234 606/1 |
| 2010/0168766 A1* | 7/2010 | Zeng | A61B 17/3403 606/130 |
| 2012/0184956 A1 | 7/2012 | Velusamy et al. | |

* cited by examiner

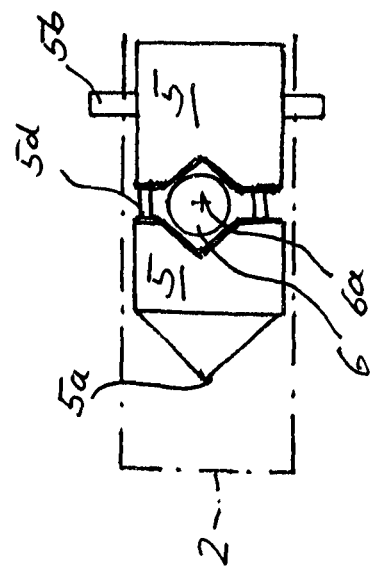
Fig. 1
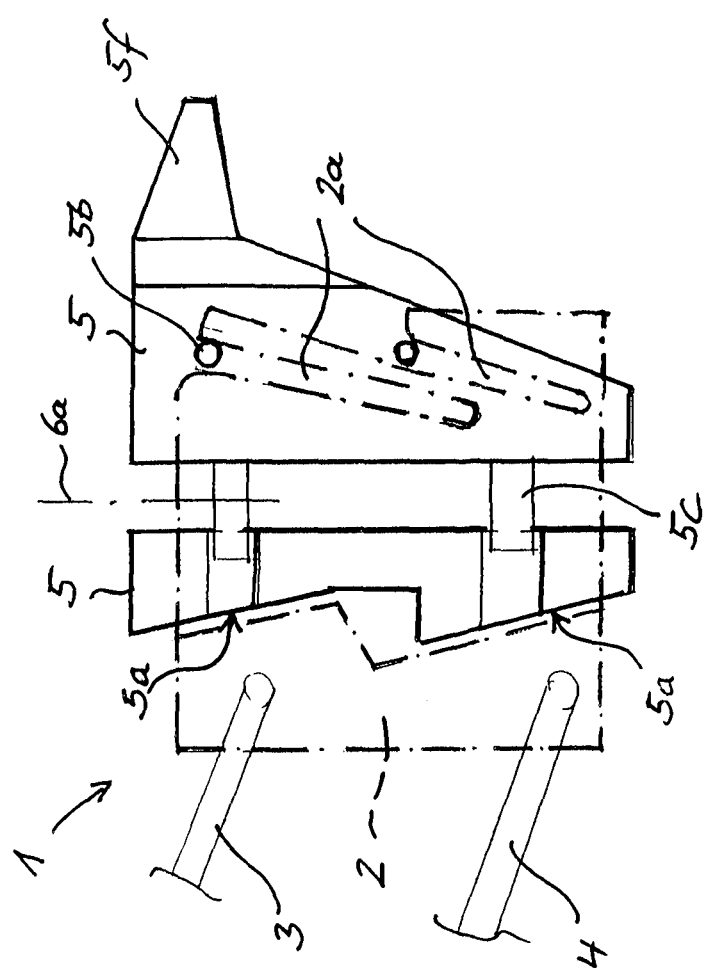
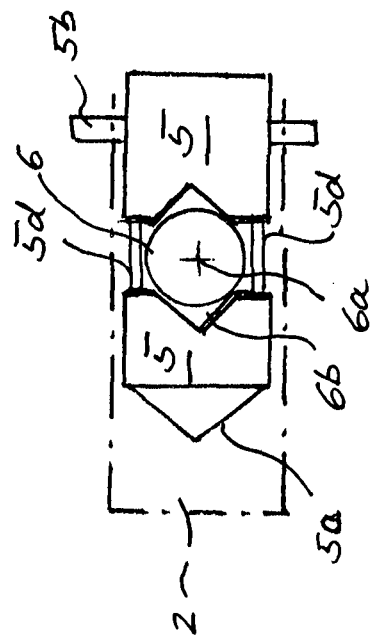

INSTRUMENT GUIDE

The invention relates to an instrument guide, especially for inserting of puncture needles in patients.

BACKGROUND OF THE INVENTION

Such a device is basically known from DE 20 2004 003 646 of the present inventor, wherein this targeting device has shown precise control in many surgical or stereotactic interventions on or in the human body. Especially by the use of modern computer technologies, such as computer tomography (CT) or magnetic resonance imaging, it is possible to precisely define the necessary insertion points, entrance depths and entrance directions of medical instruments, so that a target device for guiding these instruments has to comply with the increased accuracy. By means of such CT patient data and parameters an instrument can then be brought to the defined target point on or in the body. A special application with radio frequency ablation (RFA) is described in "chemiereport.at 7/11, p. 42.

Essential features of such targeting devices for guiding medical instruments are high accuracy and quick reproducibility. However, the stereotactic accuracy is reduced with repeated operations, as the device has to be changed for each instrument. Many treatments require different needle diameters, so that not only the needle sleeves must be replaced, but the target axis may shift according to puncture needles with different diameters and must therefore be re-adjusted. This also applies for the radiation therapy, in which so-called pins or seeds are directly delivered into the tumor tissue to be irradiated. Thus, it is possible to achieve significant improvements in this area by computer-based navigation systems, wherein the position of the needle tip in or on the body is displayed on the screen instead of the location of the probe tip. The request for a fast and easy reproducibility still requires improvements to the targeting device in order to maintain the exact adjustment in all spatial axes.

The above-mentioned document (or the corresponding WO 2005/084565) discloses a precise and variable guide for such medical instruments (including needles) wherein actuators, arranged above each other, permit remote control in an advantageous way. This instrument guide holder has two joints, particularly ball heads formed at the front ends of adjusting arms, which are, however, relatively difficult to change, especially when different needle sizes are required. In addition, a plurality of guide sleeves ("inserts") are needed for adapting to the respective needle diameters, being cost-increasing. Also, depending on the manufacturer different tolerances exist, so that the accuracy and sensitivity of needle advancement may suffer by slightly "sticking". This also applies for a rapid release of the needle (f. i. when the patient becomes restless), such that the needle or the instrument must be quickly retreated out of the holder.

SUMMARY OF THE INVENTION

Thus, the invention is based on the objective to provide a simple instrument guide which is particularly variable and convenient to use.

The objective is achieved by a configuration where two coupled guide jaws provide an exact centric adjustment of the needle channel. In addition, the clamping or guiding force can be adjusted or fine-tuned in an advantageous manner to adjust the advancing forces of the instrument to the respective tissue to be treated. In particular for alternating use of needles having different thickness this instrument guide is advantageous as the center of the needle channel remains exactly on one spatial line, such that for navigation no lateral adjustment to the target line is to be made. Thus, the change of different needle sizes can be carried out very rapidly which is convenient for the patient.

In addition, because the positioning in relation to a marker is clearly defined, precise pointing to previously specified targets in CT is possible so that a significant reduction of radiation exposure of medical staff and easiness of neurosurgery interventions is achieved. Further, a rapid and patient-friendly release of the instrument is achievable in an emergency.

It is suitable to fasten the base at two articulated arms at the free ends of the adjusting arms described above. However, it is also possible to hold the instrument guide with one hand. For quick snap connection pins or brackets can be provided for fast and easy coupling to the adjusting arms. The same applies for an extension of one of the guide jaws, which can be grasped easily and quickly in an emergency. The guide jaws can also be easily inserted into the body and can be adjusted sensitively, particularly by smooth-running slots or inclined guides in the base body. The needle can thus be taken up again in exactly the same orientation, especially when it is replaced by a needle of a different diameter.

Thus, the instrument guide enables the insertion of instruments in precise direction setting. The prismatic shape of the guide jaws enables precise targeting, as generally cylindrical instruments (including needles) have merely line contacts to ensure a smooth advance of the needles. In addition, friction-reducing coatings or the use of rolling elements (e.g. V-shaped rollers) can improve easiness.

BRIEF DESCRIPTION OF THE DRAWINGS

Hereinafter, a preferred embodiment is described referring to the drawings. In the drawings:

FIG. 1 is a side view of an instrument guide with associated plan views in two positions for different needle diameters;

DETAILED DESCRIPTION OF THE INVENTION

Figure 2:
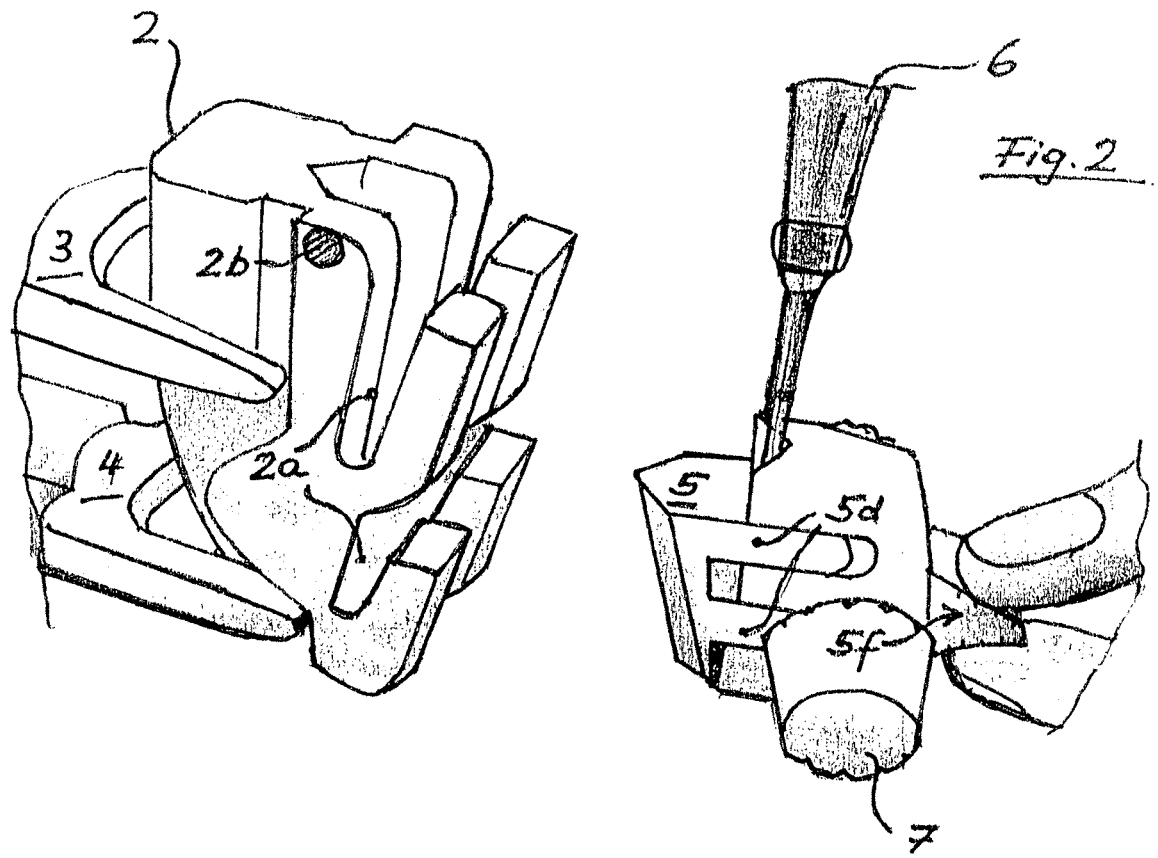
FIG. 2 is a perspective view of the instrument guide shortly before insertion into the base.

An instrument guide 1 is shown with a bracket-like base body 2 in dashed lines. The base body 2 is preferably connected to a not-shown adjusting device via adjusting arms 3 and 4, which are preferably adjustable with two actuators in accordance with the above-discussed prior art. In this way, the instrument guide 1 is set in several degrees of freedom.

The main or base body 2 houses two opposite guide jaws 5 for accommodating a needle 6 as an example of a medical instrument. The left guide jaw 5 has two guide ways 5a that are mutually parallel inclined at an angle of approximately 15° to the central axis 6a of the needle 6. However, also only one guide way 5a might be sufficient (cf. FIGS. 2 and 3). The right guide jaw 5 has two pins 5b, which engage in corresponding guide slots 2a on the base body 2, wherein the slots 2a have the same inclination as the guide ways 5a, but in mirror image alignment to the middle plane that contains the central axis 6a. In this way, a synchronous adjustment is achieved in centric relation to the central axis 6a by the coupling of the two guide jaws 5 via at least one follower 5c, here in the form of two pins 5d. When pressing one guide jaw 5 (in particular here the easily accessible right one) the other guide jaw 5 follows, thus ensuring the exact same distance from the central axis 6a, so that on replacing the needle 6 (here in plan view on the left with a relatively large diameter) to a thinner needle 6 (here shown at the bottom right in plan view) a precise alignment in the central axis 6a is maintained as both guide jaws 5 are synchronously adjusted towards the central axis 6a. This follower coupling of the guide jaws 5 can also be obtained with eccentrics, parallelograms, or similar mechanisms.

As shown in the associated plan views in FIG. 1, the guide jaws 5 have a prismatic shape or a V-shaped groove towards the needle 6, each to form a needle channel 6b. The back of the left guide jaw 5 or guide way 5a is designed in an arrow shape to provide high lateral support and to ensure accuracy during the adjustment (cf. FIGS. 2 and 3). These mentioned areas may have a low-friction coating to increase the ease of operation. The needle channel 6b may also include rollers or V-shaped rollers, so as to facilitate the advancement of larger instruments (such as drills in bone surgery). The base body 2 and the guide jaws 5 are preferably made of plastics, transparent to X-rays.

Figure 3:
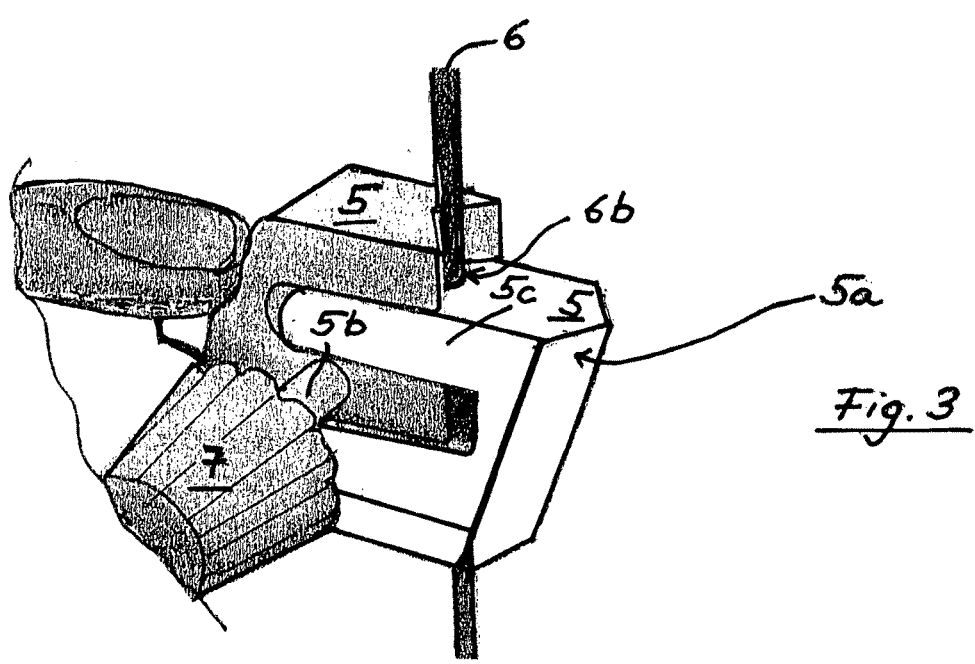
FIG. 3 shows a detail view of two nested guide jaws.

FIGS. 2 and 3 show the followers in the form of two pins 5d as well as locking nuts 7 on the pins 5b. By tightening them, the degree of clamping force can be adjusted for allowing the free movement of the needle 6. In addition, an extension 5f of the guide jaw 5 is easy to grip (cf. illustrated thumb and finger). Thus, the guide jaws 5 can be easily inserted in the base body 2, as indicated in FIG. 2.

Since the projection or extension 5f is arranged opposite to the adjusting arms 3 and 4, the "external" guide jaw 5 can be rapidly taken out of the needle channel 6b in an emergency, so that the needle 6 is released then. This guide jaw 5 can also be designed as a clamp, which is released by vigorous squeezing between thumb and finger out of the locking engagement with the base body 2.

In FIG. 2 some depressions are shown on the outer side of the base body 2, for accommodating markers 2b (only one indicated) for referencing or navigation purposes.

These markers 2b can also be provided on a separate linkage that is attached adjacent to the base body 2. In addition, the base body 2 may also include drives (e. g. fine thread spindles) to advance an instrument or the needle 6 along the central axis 6a.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. An instrument guide for inserting of puncture needles into patients, the instrument guide comprising:
    a base body pivotably mounted in plural axes on two adjusting arms;
    a needle channel having a central axis; and
    two or more guide jaws coupled to one another and centrally adjustable,
    wherein at least one of the two or more guide jaws has at least one laterally projecting pin for coupling to the base body, and
    wherein the instrument guide comprises at least an inclined guide way and a slot, inclined in the same way, but in mirror image alignment to a middle plane that comprises the central axis, the inclined guide way and slot is for guiding the at least one laterally projecting pin on centric adjustment of the needle channel, thus maintaining the central axis.

2. The instrument guide according to claim 1, wherein the guide jaws have a prismatic shape with formation of the needle channel as a double V-shaped needle channel.

3. The instrument guide according to claim 1, wherein at least one of the two or more guide jaws has an arrow shape directed towards the base body.

4. The instrument guide according to claim 1, wherein at least one of the two or more guide jaws is a clamp.

5. The instrument guide according to claim 1, wherein the at least one laterally projecting pin carries a locking nut.

6. The instrument guide according to claim 1, wherein one of the two or more guide jaws has a protruding, slightly tangible extension for quick release of the guide jaw.

7. The instrument guide according to claim 1, wherein the two or more guide jaws are coupled with at least one follower means in the form of pins.

8. The instrument guide according to claim 1, wherein the base body or a structure adjacent thereto has at least one marker element for image referencing or navigation.

9. The instrument guide according to claim 1, wherein the clamping force of the two or more guide jaws is adjustable.

10. The instrument guide according to claim 1, wherein the base body or a member connected thereto has a scaling and/or stop for adjustment of the needle penetration depth.

11. The instrument guide according to claim 1, wherein the two or more guide jaws for the needle channel are formed in a friction-reducing manner with cylindrical rollers or V-shaped rollers.

12. The instrument guide according to claim 1, wherein the needle channel has an outer diameter, and wherein the inclined guide way and slot is for guiding the at least one laterally projecting pin on centric adjustment of the outer diameter of the needle channel, thus maintaining the central axis.

* * * * *